United States Patent
Bernardin et al.

(10) Patent No.: US 8,541,604 B2
(45) Date of Patent: Sep. 24, 2013

(54) PROCESS FOR THE FUNCTIONALIZATION OF BIOLOGICAL MOLECULES

(75) Inventors: Aude Bernardin, Bagneux (FR); David Bonnaffe, Paris (FR); Isabelle Texier-Nogues, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 298 days.

(21) Appl. No.: 12/905,393

(22) Filed: Oct. 15, 2010

(65) Prior Publication Data

US 2011/0118484 A1    May 19, 2011

(30) Foreign Application Priority Data

Oct. 15, 2009    (FR) ...................................... 09 57232

(51) Int. Cl.
*C07D 311/82*  (2006.01)
*C07C 229/32*  (2006.01)

(52) U.S. Cl.
USPC ............................................ 549/214; 560/507

(58) Field of Classification Search
USPC .......................................... 549/214; 560/507
See application file for complete search history.

(56) References Cited

PUBLICATIONS

Ning et al, Angewandte Chemie International Ed., vol. 49, p. 3065-3068, Apr. 12, 2010.*

* cited by examiner

*Primary Examiner* — Bernard Dentz
(74) *Attorney, Agent, or Firm* — Scully, Scott, Murphy & Presser, P.C.

(57) ABSTRACT

The present invention is targeted at a novel coupling method of 1,3-dipolar cycloaddition type which is of particular use for the functionalization of biological molecules, such as, for example, proteins, enzymes or nucleic acids, insofar as it can be carried out in an aqueous medium and at ambient temperature.

17 Claims, 2 Drawing Sheets

PROCESS FOR THE FUNCTIONALIZATION OF BIOLOGICAL MOLECULES

The present invention is targeted at providing a novel coupling method which is of particular use for the functionalization of biological molecules, such as, for example, proteins, enzymes or nucleic acids, insofar as it can be carried out in an aqueous medium and at ambient temperature.

Coupling reactions are a functionalization route which is widely used, in particular in the field of chemistry, from the viewpoint of their high specificities.

This is because, by being based on the interactivity of two specific groupings respectively carried by the two entities which it is desired to couple, these reactions make it possible to significantly reduce the risk of side reaction(s) and generally guarantee a satisfactory yield of expected coupling product.

However, the achievement of this coupling reaction is generally dependent on, in addition to bringing together the compounds carrying the two reactive groups, the adjustment of additional parameter(s). These parameters can be physical parameters, such as temperature, atmospheric pressure, pH, indeed even exposure to UV radiation, for example, or be of chemical nature, such as the presence of a catalyst.

It is in particular from the viewpoint of the need to consider some of the parameters mentioned above that there exist rather few coupling reactions which can be used under biological conditions (in vitro or in vivo).

For obvious reasons, some parameters are not compatible with use in a biological medium, such as, for example, a highly acidic pH.

Furthermore, a coupling reaction carried out in a biological medium or with regard to a biological molecule imposes additional constraints: none of the reactants or products of the reaction must be toxic; the products and reactants must be biologically inert with regard to the functional groups of the living being: carboxylic acids, amines, thiols, and the like, in order to obtain a better coupling specificity; the reaction must take place rapidly in an aqueous medium, at physiological pH and physiological temperature, and, if possible, must not be dependent on the concentration of salts present in the medium (Na, Cl, Mg, K, and the like) and the reaction must be effective at a low concentration.

Mention may however be made, as coupling reactions which can be carried out with molecules of biological nature, of those based on the interactivity of aldehyde/ketone groups with hydrazide/aminooxy groups.

Ketone and aldehyde groups have indeed been widely used to bring about modifications of biomolecules by incorporating them during syntheses (or biosyntheses) in the form of modified monomers (sugars, amino acids, and the like). These groups then make possible subsequent modification by reacting them with hydrazines or aminooxys, assembling of two inhibitor parts, labeling with contrast agents, and the like [1].

Unfortunately, the use of ketone and aldehyde groups is limited by the biological medium itself. This is because carbonyl groups also react with amines and are not specific with regard to the biological molecules comprising them. Furthermore, the optimal pH of this condensation reaction is 5-6; the reaction is thus either very slow or the acidification of the medium results in a degree of cell death or in the decomposition of sensitive biomolecules.

Another type of coupling reaction which has been considered for in vivo chemistry [2] is a reaction which is based on the interaction of an azide with either a phosphine (Staudinger reaction) or an alkyne (Huisgen 1,3-dipolar cycloaddition).

The azide group proves to be advantageously inert with regard to the functional groups encountered in the world of the living being, highly energetic and not very reactive with regard to a large number of groups.

Unfortunately, the major curb on the use of the first type of interaction is the employment of a phosphine which can be easily oxidized in the air.

With regard to the Huisgen cycloadditions with azide groups, they are only possible ex vivo from the viewpoint of the fact that they require the use of copper salts, ruled out in vivo due to their toxicity.

It is admittedly possible to dispense with the presence of copper by activating the alkynes with electron-withdrawing groups; however, these compounds are then capable of undergoing Michael reactions in a biological medium rich in nucleophiles. Another alternative for accelerating the 1,3-dipolar cycloaddition of azides to alkynes consists in carrying out the reaction on strained multiple bonds, the ring strain being the driving force of the reaction (and replacing the catalysis). The Bertozzi group has thus taken advantage of the acceleration of the reaction due to the ring strain to develop a (3+2) cycloaddition between azides and cyclooctynes which takes place under physiological conditions and without apparent toxicity, in order to be able to carry out chemical modifications on the cells in a living organism [3-4].

Unfortunately, azides, by proving to be sensitive to photodecomposition and by, some of them, being potentially explosive, do not turn out to be very compatible for use in a biological medium.

In point of fact, from the viewpoint of their selectivity, 1,3-dipolar cycloadditions obviously constitute a functionalization route which it would be particularly advantageous to be able to take advantage of in a biological medium.

As an alternative to azide/alkene 1,3-dipolar cycloadditions, there exist nitrone/alkene 1,3-dipolar cycloadditions. The latter make possible access to isoxazolidine derivatives, which can subsequently be converted to numerous advantageous products, in particular β-lactams, lactones, amino alcohols and keto alcohols. This reaction is very popular and provides two pairs of diastereoisomers resulting from the endo or exo approaches. The same type of reaction between nitrone and alkyne makes it possible to obtain isoxazolines, which can subsequently be subjected to various rearrangements, providing novel heterocyclic systems.

However, these 1,3-dipolar cycloadditions of nitrones to unsaturations are generally carried out, on the one hand, in an organic medium and, on the other hand, at high temperatures. As regards the first constraint, it is generally imposed by the fact that the condensation of an aldehyde and of a hydroxylamine requires anhydrous conditions in order to form the corresponding nitrone. However, it has been shown that the use of a surfactant makes it possible to form a nitrone and to carry out the one-pot cycloaddition of the latter with ethyl acrylate [5].

The present invention is based more particularly on the observation by the inventors that the interaction of a nitrone with a specific group proves to be achievable under mild conditions which are thus compatible with use in vivo, that it to say in an aqueous medium and at a temperature which can vary from ambient temperature to body temperature.

More specifically, the present invention is based on a process of use in grafting at least one molecule of interest to an additional entity comprising at least the stages consisting in having available said molecule provided, at the surface, with at least one group G1 which is reactive according to a 1,3-dipolar cycloaddition reaction, and bringing together said molecule and said entity provided, at the surface, with at least one group G2 complementary to the group G1 from the viewpoint of said 1,3-dipolar cycloaddition, under conditions favorable to said cycloaddition of said groups G1 and G2, characterized in that said groups G1 and G2 are respectively a nitrone and a strained cycloalkynyl radical or vice versa.

Within the meaning of the present invention, the expression "said groups G1 and G2 are respectively a nitrone and a strained cycloalkynyl radical or vice versa" means that the group G1 is a nitrone and the group G2 a strained cycloalkynyl radical or that the group G1 is a strained cycloalkynyl radical and the group G2 a nitrone.

The process according to the invention is advantageously compatible with use in vitro, ex vivo and/or in vivo.

Thus, said cycloaddition can be carried out and preferably is carried out in a medium comparable to a biological medium and more particularly in an aqueous medium.

According to another preferred alternative form, said cycloaddition can be carried out and preferably is carried out at ambient temperature or at body temperature.

According to yet another preferred alternative form, said cycloaddition is carried out in vivo at the surface of a tissue or within a living organism.

As emerges from the examples presented below, the inventors have found that the 1,3-dipolar cycloaddition reaction between a nitrone and a strained cycloalkyne is capable of being carried out under mild conditions compatible with biology, namely at ambient temperature, in an aqueous medium, and does not require the use of an additional additive for its activation.

Thus, the process according to the invention makes it possible in particular to dispense with the use of additives of the catalyst, base or ligand type (necessary in conventional click chemistry) and to be freed from the problems of toxicity of copper(I) or of cryptand ligands, or variations in physiological pH values damaging to cell viability, and to simplify problems of bioavailability in the case of a reaction carried out in vivo.

Furthermore, the inventors have found that the interactivity of a nitrone group for a strained cycloalkyne unit proves to be particularly advantageous from the viewpoint of that displayed by an azide group with regard to the same cycloalkyne unit.

First of all, the cycloaddition reaction between nitrone and strained cycloalkyne forms a cycloadduct which rearranges in order to release an amine which can in turn be used for the coupling of another molecule to the assembly constructed previously by the cycloaddition reaction.

In addition, the compounds comprising an azide group are potentially explosive and consequently difficult to handle, in contrast to those comprising a nitrone group.

Thus, the process according to the invention makes it possible, under conditions compatible with the living being, to graft a biomolecule of interest to another entity while preserving the conformations of the biopolymers in a general way, such as the tertiary and quaternary structures of proteins, the hybridization of DNA strands, RNA-DNA complexes, triple helical or quadruple helical DNA complex structures, and the like, which are stabilized by weak bonds, such as hydrogen bonds.

Within the meaning of the present invention, the additional entity can be another molecule of interest or a substrate.

The process according to the invention makes it possible, on the one hand, either to couple biomolecules, such as, for example, nucleic acids, proteins, enzymes, antibodies, oligosaccharides, lipids, and the like, to other molecules, such as, for example, contrast agents, radiolabeled molecules, transport vectors, ligands, indeed even another biomolecule of the abovementioned types, or to functionalize substrates, such as, for example, organic or inorganic nanoparticles, biomaterials, living tissues or nanocrystals, indeed even also to chemically modify a molecule in order to overcome, for example, its native sensitivity to temperature, to organic solvents, to basic conditions and/or to the presence of transition metals or of cryptand.

Of course, the process according to the invention is in no way limited to a use with regard to a biological environment. It also turns out to be of particular use in coupling two chemical molecules of interest, grafting a chemical molecule to a functionalized surface or grafting a biomolecule to the surface of a nanoparticle, indeed even chemically modifying living tissues.

Consequently, according to another of its aspects, the present invention relates to a process of use in functionalizing the surface of a substrate with at least one molecule of interest comprising at least the stages consisting in:

having available said molecule provided, at the surface, with at least one group G1 which is reactive according to a 1,3-dipolar cycloaddition reaction, and bringing together said molecule and said substrate provided, at the surface, with at least one group G2 complementary to the group G1 from the viewpoint of said 1,3-dipolar cycloaddition, under conditions favorable to said cycloaddition of said groups G1 and G2, characterized in that said groups G1 and G2 are respectively a nitrone and a strained cycloalkynyl radical or vice versa.

According to an alternative embodiment, said substrate is a material dedicated to a biological use.

It can in particular be a DNA chip or a cell for high-throughput screening tests (enzymatic activities, tests for cytotoxicity of anticancer agents, antibacterials, and the like).

Such a process is also of particular use in the functionalization of specific polymers and/or of biopolymers and in the synthesis of structures of dendritic type, of hydrogels, of phospholipids, of lipids or of lipid nanoparticles, such as liposomes, nanocapsules, SLNs (Solid Lipid Nanoparticles) or lipid nanoemulsions.

According to yet another of its aspects, the present invention relates to a process of use in coupling two molecules of interest comprising at least the stages consisting in:

having available a first molecule of interest provided, at the surface, with at least one group G1 which is reactive according to a 1,3-dipolar cycloaddition reaction, and bringing together said molecule and said second molecule of interest provided, at the surface, with at least one group G2 complementary to the group G1 from the viewpoint of said 1,3-dipolar cycloaddition, under conditions favorable to the cycloaddition of said groups G1 and G2, characterized in that said groups G1 and G2 are respectively a nitrone and a strained cycloalkynyl radical or vice versa.

Such a process is of particular use in the synthesis of polyfunctionalized molecules for therapeutic purposes or the labeling of cells or of living tissues by contrast agents.

Thus, according to yet another of its aspects, the present invention relates to a process of use in the labeling of a molecule of interest or of a substrate by a contrast agent comprising at least the stages consisting in:

having available said molecule of interest or said substrate provided, at the surface, with at least one group G1 which is reactive according to a 1,3-dipolar cycloaddition reaction, and bringing together said molecule of interest or said substrate and said contrast agent provided, at the surface, with at least one group G2 complementary to the group G1 from the viewpoint of said 1,3-dipolar cycloaddition, under conditions favorable to the cycloaddition of said groups G1 and G2, characterized in that said groups G1 and G2 are respectively a nitrone and a strained cycloalkynyl radical or vice versa.

Such a process is of particular use in the labeling of cells or living tissues.

Within the meaning of the present invention, "grafting" covers the two reactions which follow, namely:

"anchoring", which refers to the immobilization of a compound, in this case a molecule of interest, at the surface of a substrate, and the term "coupling", which describes the reaction between at least one end functional group of a first compound, in particular a first molecule of interest, and at least one complementary functional group carried by a second molecule of interest.

According to an alternative embodiment, the process according to the invention is employed for the purposes of anchoring molecule(s) of interest at the surface of a material of substrate type.

This substrate can, for example, be a solid or semisolid support. It can be chosen from surfaces of metal, semiconductor, oxide, such as aluminas, or $TiO_2$, organic and biological type.

It can in particular be a support suitable for use as nucleic acid (DNA, RNA, oligonucleotides), protein, sugar or cell chip or as photosensitizer for photovoltaic cells, or optical label of silica beads (for suspended chips) or else a biological support of biological tissue or cell type.

These supports or their surfaces to be functionalized can optionally be nanostructured.

Thus, the support can be composed of particles, preferentially with a diameter of between 5 nm and 10 μm and more preferably still between 5 nm and 300 nm. These particles can be inorganic or organic. Mention may be made, among inorganic materials, of nanoparticles of metal (for example: gold or silver), semiconductor (for example: silicon, CdSe, CdTe, CdSeTe, InP, InAs, PbS or $CuInS_2$) or oxide (for example: iron oxides, aluminas, $TiO_2$ or $SiO_2$) type. Mention may be made, among nanoparticles of organic type, of natural and synthetic nanoparticles of polymers or of biopolymers, structures of dendritic type, hydrogels or lipid nanoparticles, such as liposomes, nanocapsules, SLNs (Solid Lipid Nanoparticles) or nanoemulsions.

Mention may in particular be made, as example of molecules of interest, of labels, colorants, fluorophores (such as, for example, coumarins, fluorescein, modified fluoresceins, rhodamines, guanines, boron-dipyrromethene, oxazines and others), radiolabeled molecules, contrast agents (X-ray, MRI), toxins (including cytotoxins), linkers, therapeutic, cosmetic or plant-protection active principles, members of a specific binding pair, peptides, amino acids and amino acid residues, polypeptides (including peptides and proteins), sugars and sugar residues, photosensitizers, such as, for example, eosin, rose bengal, phthalocyanines, chlorins, bacteriochlorins or porphyrins, such as, for example, tetrakis[meso(4-ethynylphenyl)porphyrin, 1,10-(4-ethynylphenyl)-5,15-(4-mesityl)porphyrin and 1-(4-ethynylphenyl)-5,10,15-(4-mesityl) porphyrin, the presence of which on a surface is of particular use in the field of molecular electronics and light therapy, or compounds exhibiting cis-trans isomerism, such as diarylethylene derivatives, spiropyrans, spiroxazines, fulgides or azobenzene (the presence of which on a surface is of particular use in the manufacture of light-controlled molecular switches).

According to a preferred alternative form, the molecule of interest is a biological molecule.

The process of the invention can comprise bringing together a strained cycloalkynyl group present in the substrate and a nitrone group present in the molecule of interest.

However, the process according to the invention generally comprises bringing together a nitrone group present in the substrate and a strained cycloalkynyl group present in the molecule of interest.

The biomolecules of interest can be of natural origin or produced synthetically or recombinantly and can be isolated or purified.

When the molecule of interest is a polypeptide, the polypeptide can be composed of D- or L-amino acids or both and can in addition be modified, whether naturally, synthetically or recombinantly, in order to include other groups therein. For example, the target polypeptide can be a lipoprotein, a glycoprotein or any other modified protein.

According to another alternative embodiment, the process according to the invention is carried out in order to couple at least two molecules of interest, in particular as defined above.

According to another alternative embodiment, the molecule or one of the molecules of interest is a contrast agent.

Strained Cycloalkynyl

Within the meaning of the present invention, the term "strained cycloalkynyl" extends to heterocycloalkynyls which can comprise, if appropriate, a nitrogen, oxygen, sulfur, phosphorus or silicon atom. More particularly, an 8- or 9-membered ring is involved.

According to a preferred form of the invention, the cycloalkynyl group is a cyclooctynyl group.

The strain applied to the cycloalkynyl group can be increased in various ways, for example by the use of heteroatoms, the degree of unsaturation, the bending due to twisting, the use of electronn-withdrawing groups, and the like. The corresponding derivatives are also covered under the term "strained cycloalkynyl".

Thus, the strained cycloalkynyl in accordance with the invention can be a compound in which one or more carbon atom(s) of the cycloalkynyl ring, with the exception of the two carbon atoms joined by a triple bond, is substituted by one or more electron-withdrawing group(s), for example a halo (bromo, chloro, fluoro or iodo) group, a nitro group, a cyano group or a sulfone group. The electron-withdrawing group is preferably positioned α to the triple bond.

Mention may non-exhaustively be made, as other group capable of being present on the cycloalkynyl, of carboxyl, amine (for example alkylamine (for example lower alkylamine) or arylamine), ester (for example alkyl ester (for example lower alkyl ester or benzyl ester), aryl ester or substituted aryl ester), thioester, sulfonyl halide, alcohol, thiol, succinimidyl ester, isothiocyanate, iodoacetamide, maleimide or hydrazine groups, and the like.

The functionalization of a molecule of interest or of a substrate with such a cycloalkynyl group clearly comes within the competences of a person skilled in the art.

Generally, this cycloalkynyl group is covalently bonded via a spacer arm to the molecule of interest or the substrate under consideration.

According to a specific embodiment, this spacer arm can have the formula as follows:

—X-E-A-G  (I)

in which:
X, bonded to the molecule of interest or the additional entity under consideration, is the reaction product of two reactive functional groups, such as, for example, thiol/maleimide, amine/activated carboxylic acid or carbonyl/oxyamine, E is an organic spacer group, A represents a single bond or a group chosen from —CONH—, —NHCO—, —OCH$_2$CONH—, —NHCOCH$_2$O—, —O— or —S—, and G is the strained cycloalkynyl group.

The group E can be a hydrocarbon group comprising one or more unsaturations, for example of the alkene type. An example of such a group can be an alkylene group as defined above interrupted by one or more alkene unsaturations. When the group E comprises at least two unsaturations, it can confer, on the compounds, an ability to crosslink.

The group E can also be a poly(ethylene)glycol (PEG) chain. Such a group makes it possible to improve the solubility of the molecule of interest or of the substrate under consideration, indeed even that of the expected coupling product.

This alternative embodiment of E is particularly advantageous in the functionalization of materials of the following types: polymers, dendrimers, oligomers, lipid particles or hydrogels, capable, for example, of encapsulating fluorescent semiconductor nanocrystals, fluorophores or any other agent of diagnostic or therapeutic interest in materials, gels or formulations (plastics for optics and electronics, delivery of light-therapy agents, for example) or of acting as matrix-support for tissue reconstruction.

The group E can also be a hydrocarbon group comprising one or more aromatic groups. Mention may be made, for example, of a group comprising aromatic groups conjugated with linear unsaturated groups, such as a group resulting from the sequence of a phenylene-vinylene unit. These groups contribute to conferring nonlinear optical properties.

The group E can also be a small organic molecule which makes it possible to introduce the complementary reactive functional group, for example ethylenediamine, glycolic acid, cysteamine or any other organic molecule which makes it possible to introduce acids/amines/thiols.

Mention may also be made of a group comprising pyrrole and/or thiophene units. These groups contribute to conferring, on the material, electron-conducting properties. Mention may be made, for example, of a group comprising one or more aromatics substituted by one or more aromatic groups, such as a group comprising a sequence of quinone units or of diazo units. These groups contribute to conferring, on the compound possessing them, photo/electroluminescence properties.

Nitrone

The synthesis of nitrone groups comes within the competences of a person skilled in the art.

For example, one of the reactions conventionally considered for forming such a group is the condensation of an N-monosubstituted hydroxylamine with a ketone or an aldehyde.

In the event that such a group cannot be generated directly on one of the molecules of interest under consideration in the process of the invention, this group can be created at the surface of said molecule via the interaction of a reactive functional group of said molecule of interest with a complementary reactive functional group appearing on the additional entity carrying said nitrone group.

Thus, according to a specific alternative form of the invention, the nitrone group can be bonded to said molecule of interest via an organic spacer arm E as defined above and preferably of C$_3$ to C$_{10}$ hydrocarbon nature or a polyethylene glycol chain.

As specified above, the cycloaddition reaction is advantageously obtained without catalyst or other additives.

The activation energy necessary for the reaction is provided by the nitrone group and the strained cycloalkynyl group.

The cycloaddition can advantageously be carried out in an aqueous medium and at ambient or body temperature, i.e. a temperature varying from 16 to 45° C.

Within the meaning of the invention, an aqueous medium denotes pure water or a mixture predominantly formed of water and additionally comprising one or more additional solvents. Such mixtures are comparable to pure water.

Within the meaning of the invention, ambient temperature can vary from 16 to 28° C. and preferably from 18 to 25° C.

Within the meaning of the invention, the term "body temperature" is understood to mean temperatures of between 32 and 45° C., more particularly between 36 and 42° C. and essentially approximately from 37 to 38° C.

Thus, the process according to the invention can advantageously be carried out in vivo in a living tissue or organism.

The processes according to the invention have multiple applications, whether in synthesis, in research or in diagnosis.

The research applications also comprise the discovery of a medicament or screening applications: like any contrast agent, the invention makes possible the visualization of molecules of interest (receptor, glucose, antigen, and the like) or of biological mechanisms (endocytosis, neoangiogenesis, apoptosis, enzymatic activities, and the like) and thus makes possible the identification of therapeutic targets.

It also makes it possible to monitor the effects of a medicinal treatment (for example cytotoxic, inhibitor in an enzyme, and the like) or the detection of tumors (via specific labels).

Mention may be made, as other applications of interest, of the study of the functional and physical characteristics of a receptor, proteomics, metabolomics, and the like.

The invention can also be used in the development of matrices for tissue reconstruction (hydrogels, synthetic biomaterials or surface modification of implantable materials) and generally in the development of medical devices.

The invention can also be used in the manufacture of functionalized nanoparticles (organic or inorganic nanoparticles). These nanoparticles can be employed, for example, in the delivery of therapeutic active principles, as medical diagnostic tools or in the guidance of the surgical procedure. Mention may in particular be made, as diagnostic tool, of their use in molecular imaging.

For some applications in the medical or preclinical field, such as, for example, molecular imaging, the coupling reaction between the entity carrying the nitrone group and that carrying the strained cycloalkyne group can be carried out ex vivo or in vivo after injection, simultaneous strained or delayed in time, of the two entities.

BIBLIOGRAPHIC REFERENCES

1. Mahal, L. K. et al., Science, 1997, 276(5315), pp 1125-1128.
2. Agard, N. J. et al., Acs Chemical Biology, 2006, 1(10), pp 644-648.
3. Agard et al., Journal of the American Chemical Society, 2004, 126(46), pp 15046-15047.
4. Bertozzi, C. R. et al., Compositions and methods for modification of biomolecules, 2006, pp 1-58.
5. Chatterjee, A. et al., Organic Letters, 2003, 5(21), pp 3967-3969.

The examples and figures which follow are presented by way of illustration and without implied limitation of the range of the invention.

EXAMPLE 1

Cycloaddition Between a Nitrone and a Strained Cycloalkyne Derivative in a Nonbiological Medium

1. Synthesis of N-(propylidene)methylnitrone (4)

725 µl of propionaldehyde 2 (10 mmol) are added to a mixture of N-methylhydroxylamine (835 mg, 10 mmol) in ethanol (15 ml) and NaOMe (540 mg, 10 mmol). The combined mixture is stirred at AT for 1 h. The solution is evaporated to dryness, the residue is resuspended in $CH_2Cl_2$, the suspension is filtered and the filtrate is purified by chromatography on silica gel ($CH_2Cl_2$/MeOH 0-10%) in order to obtain the nitrone 4 in the form of a yellow solid with a weight of 500 mg. The yield is 57%.

$^1$H NMR (CDCl$_3$, 200 MHz): δ (ppm) 1.02 (t, J=7.5 Hz, 3H, H$_3$); 2.40 (dqd, J=1.0-7.5-6.0, 2H, H$_2$); 3.59 (d, J=1.0, 3H, H$_4$); 6.62 (t, J=6.0, 1H, H$_1$).

2. Synthesis of cyclooct-1-yn-3-glycolic acid (18)

a) Synthesis of 8,8-dibromobicyclo[5.1.0]cyclooctane (16)

3.65 g of cycloheptene 15 (38 mmol) and then 8.52 g of t-BuOK (76 mmol) and 9 ml of anhydrous pentane are introduced into a dry round-bottomed flask under argon. The solution, placed in an ice/salt bath (T<−5° C.), is vigorously stirred and then 4.9 ml of bromoform (57 mmol) are added dropwise. Once the addition is complete, the mixture is allowed to return to AT overnight, under argon and with vigorous stirring. Approximately 50 ml of water are subsequently added and the pH is neutralized with 1M HCl. The organic and aqueous phases are separated; the aqueous phase is extracted with 3×20 ml of pentane and the pentane phase is washed with 3×20 ml of water. After drying over MgSO$_4$, the solvent is evaporated under vacuum to give an orangey-yellow oil. The product 16 is subsequently purified by filtration through silica with, as eluent, a cyclohexane/5% AcOEt mixture. A colorless oil with a total weight of 9.10 g is then obtained, equivalent to a yield of 90% (litt. 52-65% for 9,9-dibromobicyclo[6.1.0]nonane). R$_f$ (cyclohexane 95/AcOEt 5)=0.85.

$^1$H NMR (CDCl$_3$, 400 MHz): δ (ppm) 1.05-1.22 (m, 3H, H$_{4-2-6}$); 1.34 (qq, J=1.0-7.5 Hz, 2H, H$_{3-5}$); 1.68 (ddd, J=1.5-4.0-10.5 Hz, 2H, H$_{1-7}$); 1.76-1.92 (m, 3H, H$_{4'-3'-5'}$); 2.23 (dtq, J=14.0-6.0-1.0 Hz, 2H, H$_{2'-6'}$).

b) Synthesis of methyl 2-bromocycloct-1-en-3-glycolate (17)

3.85 g of silver perchlorate (18.6 mmol) are added to a solution of 8,8-dibromobicyclo[5.1.0]octane 16 (2.5 g, 9.3 mmol) and methyl glycolate (6.35 ml, 83.9 mmol) dissolved in 5 ml of anhydrous toluene in a dry round-bottomed flask under Ar protected from light by an aluminum film. The reaction mixture is stirred at ambient temperature for 1 h 30 and then the silver salts are filtered off through a sintered glass funnel and washed with AcOEt. The solution is concentrated under vacuum to give a viscous brown oil which is purified by chromatography on silica gel (cyclohexane/2-15% AcOEt) to produce 17 in the form of a yellow oil (w=1.7 g, i.e. 66% yield).

$^1$H NMR (CDCl$_3$, 200 MHz): δ (ppm) 0.7-2.2 (m, 8H, H$_{4-4'-5-5'-6-6'-7-7'}$); 2.28 (m, 1H, H$_8$); 2.70 (ddd, J=5.0-11.5-23.5 Hz, 1H, H$_{8'}$); 3.72 (s, 3H, OMe); 3.94 (d, J=16.5 Hz, 1H, $H_9$); 4.10 (dd, J=5.0-10.0 Hz, 1H, $H_3$); 4.23 (d, J=16.5 Hz, 1H, $H_{9'}$); 6.20 (dd, J=4.0-11.5 Hz, 1H, $H_1$).

b) Synthesis of cyclooct-1-yn-3-glycolic acid (18)

150 μl of 1,8-diazabicyclo[5.4.0]undec-7-ene (DBU, 1 mmol) are added to a solution of methyl 2-bromocyclooctene-3-glycolate 17 (0.5 mmol) in anhydrous DMSO at 60° C. After stirring for 15 min, an additional 600 μl of DBU (4 mmol) are added and then the combined mixture is stirred overnight at 60° C. The mixture is acidified with 1M HCl and extracted with AcOEt. The organic phase is filtered through a separating filter and is concentrated under vacuum. The cyclooct-1-yn-3-glycolic acid 18 is purified on a preparative plate ($CH_2Cl_2$/MeOH 9/1) and is obtained with a yield of 55% (w=50 mg).

$^1$H NMR ($CDCl_3$, 200 MHz): δ (ppm) 1.3-2.3 (m, 10H, ring); 4.45 (d, J=17.0 Hz, 1H, $H_9$); 4.50 (m, 1H, $H_3$); 4.58 (d, J=17.0 Hz, 1H, $H_{9'}$); 8.12 (s, 1H, $H_{11}$).

3. Cycloaddition

The nitrone 4 (33 mg, 0.38 mmol) is added to a solution of 18 (70 mg, 0.38 mmol) in a water/THF (1 ml/200 μl) mixture. The combined mixture is stirred at AT for 2 days. The product is then extracted with $CH_2Cl_2$ and concentrated under vacuum. The expected product is too polar to be purified on silica gel and the analyses are carried out on the crude reaction product, which reveals a highly predominant product.

The reaction yield, assessed by measurement of the degree of conversion by NMR, is approximately 85% (calculated from the residual $CH_{Nit}$ peak).

22a

22b $^1$H NMR ($CDCl_3$, 200 MHz) 22a or b: δ (ppm) 0.8-2.3 (m, 13H, ring+$H_{13}$); 2.3-2.6 (m, 2H, $H_{12-8}$); 2.8-2.8 (m, 1H, $H_{12'}$); 3.6-3.8 (m, 1H, $H_3$); 3.8-4.3 (m, 2H, $H_{9/9'}$); 8.30 (s, 1H, NH).

$^{13}$C NMR ($CDCl_3$, 200 MHz) 22a or b: δ (ppm) 9.60 ($C_{13}$); 19.81 ($C_{12}$); 20.51; 22.57; 27.95; 31.70 ($C_{5-8}$); 44.27 ($C_4$); 44.36 ($C_{14}$); 66.42 ($C_3$); 79.48 ($C_9$); 133.72 ($C_2$); 135.83 ($C_{11}$); 173.26 ($C_{10}$); 213.69 ($C_1$).

Mass $ESI^+$ m/z $[M-CH_2CO_2H+H]^+$=212.4 for 212.2.

EXAMPLE 2

Preparation of Surfaces Functionalized by Nitrone Groups and Grafting of a Fluorescent Probe by a Cycloaddition Reaction with a Strained Cycloalkyne

1. Preparation of the Glass Slides Functionalized by Nitrones

The surfaces functionalized by nitrones are obtained via the following 4 stages:

slide 5 → MeNHOH → slide 6

The glass slides are first of all activated with a Brown solution in order to hydroxylate the surface. The silanization is then carried out in toluene in the presence of 5,6-epoxy-hexyltriethoxysilane at ambient temperature and in the presence of diethylamine to give the slides 3. The opening of the epoxide to give the 1,2-diol is carried out in an acid medium and then the aldehyde is obtained by oxidation by sodium periodate at the surface of the slides 4.

The final stage consists of the condensation of N-methyl-hydroxylamine with the aldehyde of the slides 5 in ethanol, in the presence of sodium methoxide and at ambient temperature.

The slides 6 thus obtained were characterized by their XPS (FIG. 1) and MIR-FTIR (FIG. 2) spectra.

Figure 1:
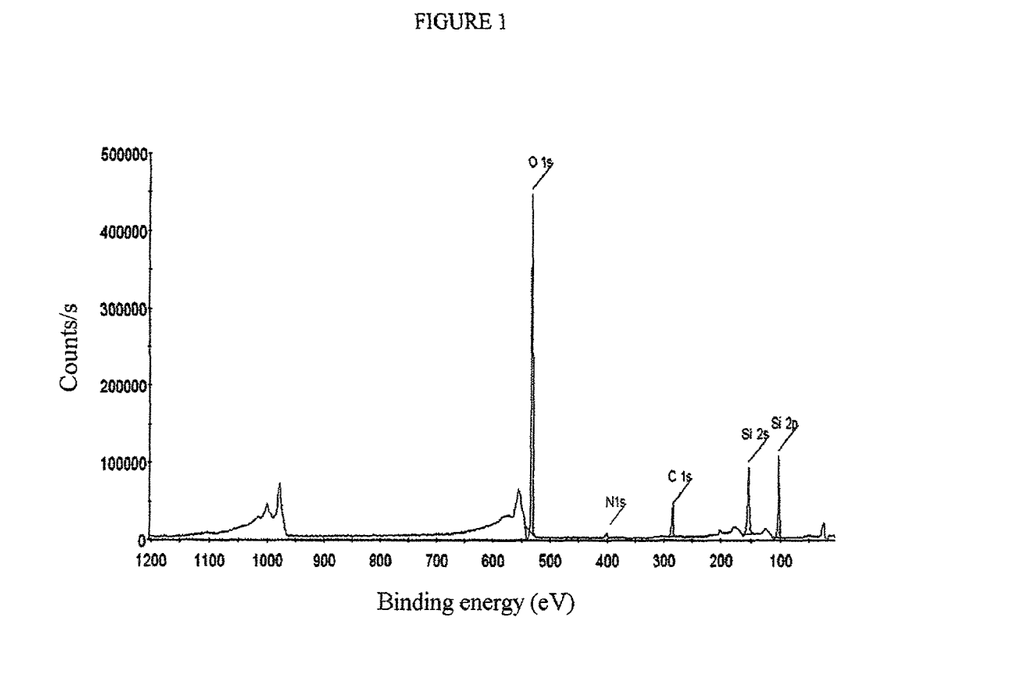
FIG. 1: Overall XPS spectrum of the substrates functionalized by nitrones.

The signals corresponding to Si (103 and 154 eV), to C (286 eV), to O (533 eV) and to N (399 eV) are present in the XPS spectrum of the slides 6. The presence of all of these signals testifies to the successful functionalization at the surface of the slides 6.

Figure 2:
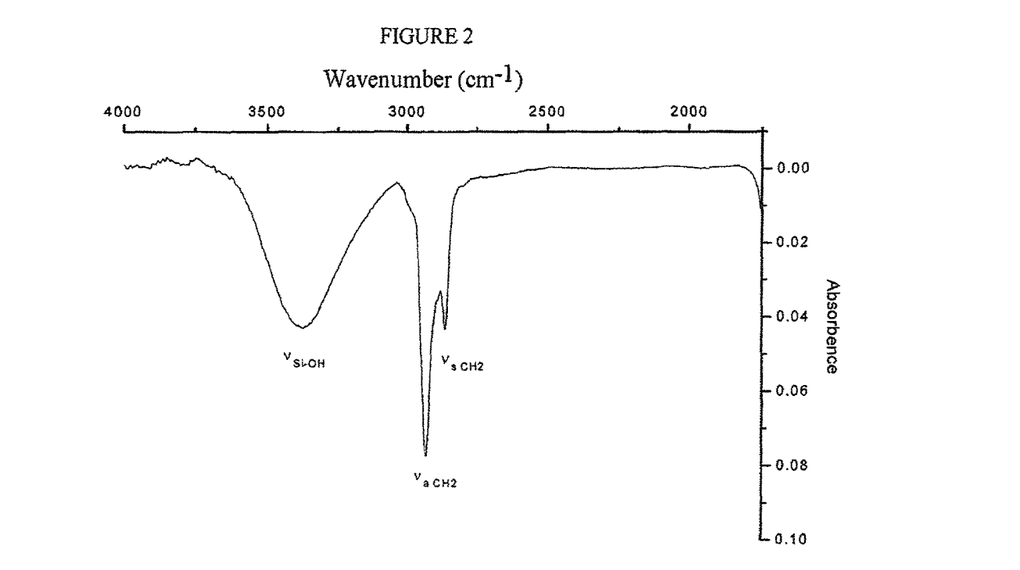
FIG. 2: MIR-FTIR spectrum of the slides functionalized by nitrones.

The functionalization of the slide is also visible, by the MIR-FTIR spectrum, in the presence of the stretching vibration bands of the $CH_2$ groups at 2931 and 2860 $cm^{-1}$.

2. Synthesis of Alexa-Cyclooctyne

1 μl of $NEt_3$ (7.4 μmol), 16 mg of EDC (1-ethyl-3-(3-dimethylamino-propyl)carbodiimide) (83 μmol), 10 mg of HOBt (N-hydroxybenzotriazole) (74 μmol) and 1 mg of Alexa 488 cadaverine 26 (1.5 μmol) (sold by Invitrogen) are added to a solution of cyclooct-1-yn-3-glycolic acid 18 (10 mg, 55 μmol) in 250 μl of a DMF/water (8/2) mixture. The reaction mixture is stirred at AT overnight and is then purified by HPLC (Appendix E). The Alexa-cyclooctyne probe 27 is obtained with a yield evaluated at 25% by UV quantification based on the Beer-Lambert law.

27

Mass ESI⁻ m/z: [M-Na]⁻=781.3 for 781.2.

3. Grafting by Cycloaddition Between the Surface Nitrone and the Fluorescent Probe Carrying a Strained Cycloalkyne 6 different concentrations of fluorescent probes were tested (in the presence of 10% of glycerol, in order to facilitate the reading of the results).

The concentrations chosen are 50, 100, 250, 500, 750 and 1000 nM. The deposition plan is represented schematically in table 1 below.

TABLE 1

| Probe 26 (control in sextuplicate) | Probe 27 (control in sextuplicate) |
|---|---|
| 50 nM | 50 nM |
| 100 nM | 100 nM |
| 250 nM | 250 nM |
| 500 nM | 500 nM |
| 750 nM | 750 nM |
| 1 μM | 1 μM |

Figure 3:
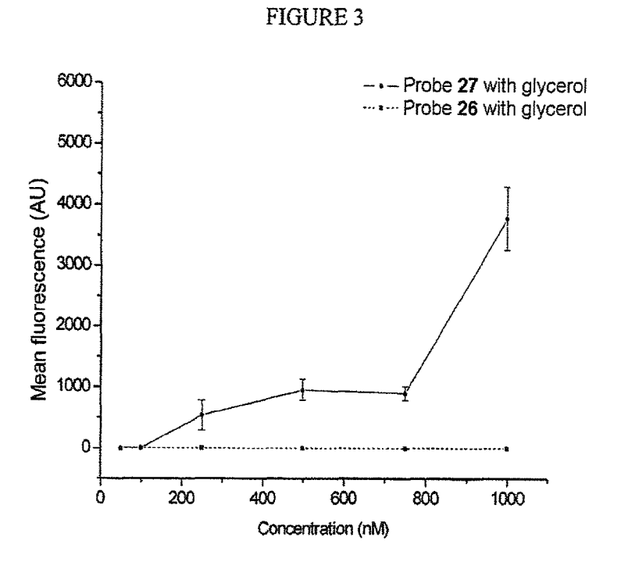
FIG. 3: Analysis of the spotting of the fluorescent probes on the slides functionalized by nitrones, means over 5 slides.

The deposition of drops of fluorescent probes was carried out on the slides 6 (functionalized at the surface by nitrone groups). The results are shown in FIG. 3.

The mean intensity of fluorescence is dependent on the concentration of fluorescent probe.

In order to confirm that the signal observed with the Alexa-cyclooctyne probe 27 on the slides is indeed due to the functionalization at the surface by chemical reaction between strained cycloalkyne and nitrone, $Si/SiO_2$ substrates functionalized with the nitrone group and incubated overnight in a solution of the Alexa-cyclooctyne probe 27 at a concentration of 250 nM were characterized by measurement of the contact angle and XPS spectrum.

The contact angles measured on $Si/SiO_2$ substrates functionalized in an identical way (carrying nitrones), before and after functionalization by chemical reaction(s) with strained alkyne, are summarized in table 2.

TABLE 2

| Substrates | $\theta_{initial}$ | $\theta_{final}$ |
|---|---|---|
| Nitrone substrate (type slide 6) | 47.3° | 53.5° |

For the surfaces of type slide 6, which are relatively hydrophilic, the grafting of a fluorophore having multiple hydrophobic aromatic rings renders the surface of the slides more hydrophobic.

In the same way, the modification of the slides 6 by incubation with the Alexa-cyclooctyne probe 27 is visible by XPS analysis.

Figure 4:
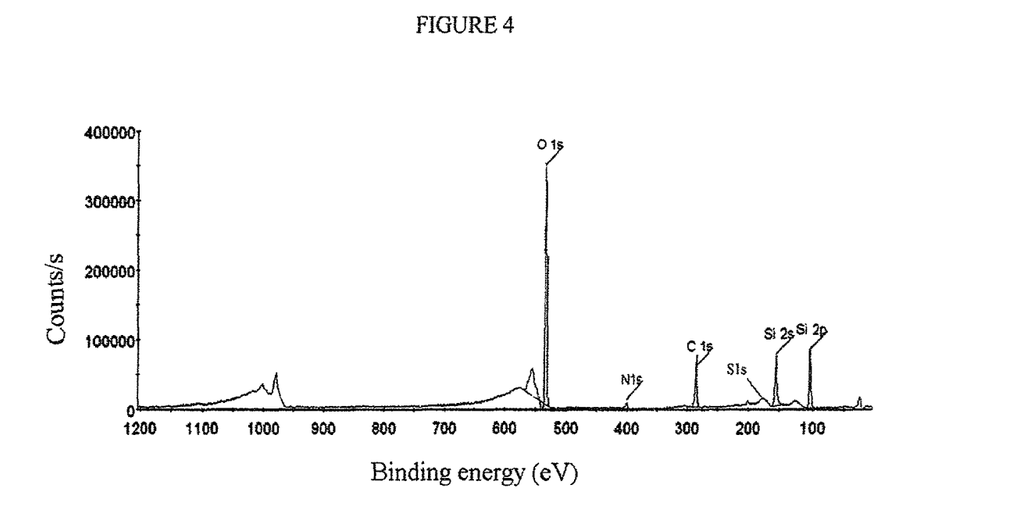
FIG. 4: Overall XPS spectrum after functionalization of the nitrone slides by cycloaddition with a strained cycloalkyne.

This analysis is reported in FIG. 4.

The signal of the nitrogen remains overall of the same form as above but with an increase in the signal at 399.6 eV, which accounts for the grafting of the Alexa-cyclooctyne probe 27 (comprising several nitrogens).

Furthermore, as shown in table 3 below, the $N/Si_{2p}$ and $C/Si_{2p}$ atomic ratios increase after the incubation with the Alexa-cyclooctyne probe 27, indicating the success of the grafting.

TABLE 3

| Atomic ratios | Before incubation | After incubation |
|---|---|---|
| $N/Si_{2p}$ | 0.043 | 0.078 |
| $C/Si_{2p}$ | 0.396 | 0.804 |

On the basis of these combined analyses of the surface of the slides after incubation with the Alexa-cyclooctyne probe 27, it can be concluded that the surface of the slides 6 has been functionalized by a [3+2]-cycloaddition reaction between nitrones and strained cycloalkynes.

The invention claimed is:

1. A process of grafting at least one molecule of interest to an additional entity comprising at least the stages consisting in
    having available said molecule provided, at the surface, with at least one group G1 which is reactive according to a 1,3-dipolar cycloaddition reaction, and
    bringing together said molecule and said entity provided, at the surface, with at least one group G2 complementary to the group G1 from the viewpoint of said 1,3-dipolar cycloaddition, under conditions favorable to the cycloaddition of said groups G1 and G2,
    wherein said groups G1 and G2 are respectively a nitrone and a strained cycloalkynyl radical or vice versa.

2. The process according to claim 1, wherein the cycloaddition is carried out in an aqueous medium.

3. The process according to claim 1, wherein the cycloaddition is carried out at ambient temperature or at body temperature.

4. The process according to claim 1, wherein said molecule of interest is chosen from labels, colorants, fluorophores, radiolabeled molecules, contrast agents (X-ray, MRI), linkers, toxins, therapeutic, cosmetic or plant-protection active principles, members of a specific binding pair, peptides, amino acids and amino acid residues, polypeptides, sugars and sugar residues, photosensitizers, porphyrins, or compounds exhibiting cis-trans isomerism.

5. The process according to claim 4, wherein the compounds exhibiting cistrans isomerism are chosen from diarylethylene derivatives, spiropyrans, spiroxazines, fulgides and azobenzene.

6. The process according to claim 1, wherein said molecule of interest is biological.

7. The process according to claim 1, wherein the additional entity is also a molecule of interest.

8. The process according to claim 7, wherein one of the molecules of interest is a contrast agent.

9. The process according to claim 1, wherein the additional entity is a substrate.

10. The process according to claim 9, wherein the substrate is chosen from surfaces of metal, semiconductor, oxide, organic and biological type.

11. The process according to claim 10, wherein the surfaces of oxide type are chosen from aluminas, $SiO_2$ or $TiO_2$.

12. The process according to claim 10, wherein the surface is nanostructured.

13. The process according to claim 1, wherein the cycloalkynyl radical is a cyclooctynyl radical.

14. The process according to claim 1, wherein the strained cycloalkynyl group is covalently bonded via a spacer arm to the molecule of interest or to the additional entity.

15. The process according to claim 14, wherein the spacer arm has the formula

—X-E-A-G  (I)

wherein:
    X, bonded to the molecule of interest or the additional entity under consideration, is the reaction product of two reactive functional groups,
    E is an organic spacer group,
    A represents a single bond or a group chosen from —CONH—, —NHCO—, —OCH$_2$CONH—, —NHCOCH$_2$O—, —O— or —S—, and
    G is the strained cycloalkynyl group.

16. The process according to claim 15, wherein E is a poly(ethylene)glycol chain.

17. A process of labeling a molecule of interest or of a substrate by a contrast agent comprising at least the stages consisting in:
    having available said molecule of interest or said substrate provided, at the surface, with at least one group G1 which is reactive according to a 1,3-dipolar cycloaddition reaction, and
    bringing together said molecule of interest or said substrate and said contrast agent provided, at the surface, with at least one group G2 complementary to the group G1 from the viewpoint of said 1,3-dipolar cycloaddition, under conditions favorable to the cycloaddition of said groups G1 and G2,
    said groups G1 and G2 respectively being a nitrone and a strained cycloalkynyl radical or vice versa.

* * * * *